US011977080B2

(12) United States Patent
Kinjo et al.

(10) Patent No.: US 11,977,080 B2
(45) Date of Patent: May 7, 2024

(54) METHOD FOR ACQUIRING INFORMATION OF TARGET POLYPEPTIDE AND REAGENT KIT

(71) Applicants: NATIONAL UNIVERSITY CORPORATION HOKKAIDO UNIVERSITY, Sapporo (JP); SYSMEX CORPORATION, Kobe (JP)

(72) Inventors: Masataka Kinjo, Sapporo (JP); Akshay Ganguly, Kobe (JP); Lausonia Ramaswamy, Kobe (JP)

(73) Assignees: NATIONAL UNIVERSITY CORPORATION HOKKAIDO UNIVERSITY, Sapporo (JP); SYSMEX CORPORATION, Kobe (JP)

( * ) Notice: Subject to any disclaimer, the term of this patent is extended or adjusted under 35 U.S.C. 154(b) by 298 days.

(21) Appl. No.: 17/241,213

(22) Filed: Apr. 27, 2021

(65) Prior Publication Data
US 2021/0333287 A1 Oct. 28, 2021

(30) Foreign Application Priority Data
Apr. 28, 2020 (JP) ................. 2020-079588

(51) Int. Cl.
G01N 33/68 (2006.01)
G01N 21/64 (2006.01)

(52) U.S. Cl.
CPC ..... *G01N 33/6803* (2013.01); *G01N 21/6428* (2013.01); *G01N 2021/6439* (2013.01); *G01N 2333/755* (2013.01); *G01N 2333/928* (2013.01); *G01N 2333/936* (2013.01)

(58) Field of Classification Search
CPC ........... G01N 33/6803; G01N 21/6428; G01N 2021/6439
See application file for complete search history.

(56) References Cited

U.S. PATENT DOCUMENTS

| 8,209,128 | B1 * | 6/2012 | Gourley | G01N 15/1429 356/417 |
| 11,698,358 | B2 * | 7/2023 | Beckman | G01N 27/44747 204/452 |
| 2003/0224469 | A1 * | 12/2003 | Buchholz | G01N 33/582 435/7.92 |
| 2004/0014134 | A1 * | 1/2004 | Kuhlemann | C12Q 1/37 435/7.1 |
| 2006/0051805 | A1 * | 3/2006 | Kato | C12Q 1/68 435/6.12 |
| 2008/0002195 | A1 | 1/2008 | Otani et al. | |
| 2009/0251690 | A1 | 10/2009 | Otani et al. | |
| 2010/0315626 | A1 | 12/2010 | Otani et al. | |
| 2015/0036145 | A1 * | 2/2015 | Cichos | G01N 21/171 356/451 |
| 2017/0304457 | A1 * | 10/2017 | Kim | A61K 9/06 |
| 2019/0091349 | A1 * | 3/2019 | Choi | C07K 16/32 |
| 2019/0154696 | A1 * | 5/2019 | Clarke | G01N 33/581 |
| 2019/0350871 | A1 * | 11/2019 | Steinmetz | A61K 9/0019 |

FOREIGN PATENT DOCUMENTS

| JP | 2008-8805 A | 1/2008 | |
| JP | 2013-64652 A | 4/2013 | |
| WO | WO-2008110581 A2 * | 9/2008 | ............... G01N 1/28 |
| WO | 2019/110977 A1 | 6/2019 | |

OTHER PUBLICATIONS

Extended European Search Report, dated Sep. 14, 2021, issued in corresponding European Patent Application No. 21170815.1.
Basak Sujit et al: "Fluorescence Correlation Spectroscopy Study on the Effects of the Shape and Size of a Protein on Its Diffusion Inside a Crowded Environment", LANGMUIR, Nov. 26, 2013, vol. 29, No. 47, (Nov. 26, 2013), pp. 14709-14717 (9 pages).
Yu Lan et al: "A Comprehensive Review of Fluorescence Correlation Spectroscopy", Frontiers in Physics, Apr. 12, 2021, vol. 9, pp. 1-21 (21 pages).
Eilon Sherman et al., "Using Fluorescence Correlation Spectroscopy to Study Conformational Changes in Denatured Proteins", Biophysical Journal, Jun. 2008, pp. 4819-4827, vol. 94.

(Continued)

Primary Examiner — Changhwa J Cheu
(74) Attorney, Agent, or Firm — Sughrue Mion, PLLC

(57) ABSTRACT

Disclosed is a method for acquiring information of a target polypeptide, comprising: acquiring a diffusion time of a fluorescently labeled target polypeptide and a diffusion time of each of a plurality of fluorescently labeled reference polypeptides by fluorescence correlation spectroscopy or fluorescence cross-correlation spectroscopy, and acquiring information on size of the fluorescently labeled target polypeptide from the diffusion time of the fluorescently labeled target polypeptide with reference to the diffusion times of the plurality of fluorescently labeled reference polypeptides, wherein information on size of each of the plurality of fluorescently labeled reference polypeptides is known, and the sizes of the plurality of reference polypeptides are different from each other.

15 Claims, 17 Drawing Sheets

(56) References Cited

OTHER PUBLICATIONS

Tingjuan Gao et al., "Characterizing diffusion dynamics of a membrane protein associated with nanolipoproteins using fluorescence correlation spectroscopy", Protein Science, 2011, pp. 437-447, vol. 20.

Oleg Krichevsky et al., "Fluorescence correlation spectroscopy: the technique and its applications", Reports on Progress in Physics, 2002, pp. 251-297, vol. 65.

R. A. Sperling et al., "Size Determination of (Bio)conjugated Water-Soluble Colloidal Nanoparticles: A Comparison of Different Techniques", The Journal of Physical Chemistry C, 2007, pp. 11552-11559, vol. 111, No. 31.

Masataka Kinjo, "Study of Protein Function Using Fluoresce Correlation Spectroscopy," Biochemistry, 2010, vol. 82, Issue 12, pp. 1103-1116 (26 pages total).

Notice of Reasons for Refusal issued Jan. 9, 2024 in Japanese Application No. 2020-079588.

* cited by examiner

| | LABELING DYE | | TARGET POLYPEPTIDE | | | DIFFERENCE FROM THEORETICAL VALUE |
|---|---|---|---|---|---|---|
| | HYDRODYNAMIC RADIUS ($R_{HC}$) (nm) | DIFFUSION TIME ($\tau_{DC}$) ($\mu$s) | | DIFFUSION TIME ($\tau_D$) ($\mu$s) | PREDICTED VALUE BY CONVENTIONAL METHOD OF HYDRODYNAMIC RADIUS ($R_H$) (nm) | PREDICTED VALUE − THEORETICAL VALUE (5.4nm) (nm) |
| Alexa 647 | 0.8 | 94 | SERUM 1 | 240 | 2.04 | −3.36 |
| | | 80 | PLASMA 1 | 276 | 2.76 | −2.64 |
| | | 98 | PLASMA 2 | 979 | 7.99 | 2.59 |
| Alexa 488 | 0.7 | 49 | SERUM 1 | 139 | 1.94 | −3.46 |
| | | 44 | PLASMA 1 | 138 | 2.20 | −3.20 |
| | | 49 | PLASMA 2 | 155 | 2.21 | −3.19 |

| vWF | | EXAMPLE 2 | | |
|---|---|---|---|---|
| THEORETICAL VALUE (nm) | DIFFUSION TIME (μs) | MEASURED VALUE (nm) | CV (%) | DIFFERENCE (nm) |
| 16.25 | 3476 | 14.0 | 4.9 | 2.3 |

|  | DIFFUSION TIME MEASURED VALUE (μs) | THEORETICAL VALUE OF HYDRODYNAMIC RADIUS (nm) |
|---|---|---|
| Thyroglobulin | 490 | 8.6 |
| β-Amylase | 287 | 5.4 |
| BSA | 230 | 3.5 |
| Carbonic anhydrase | 81 | 2.1 |
| Lysozyme | 95 | 1.9 |
| Aprotinin | 50 | 1.4 |

FIG. 10C

| | EXAMPLE 4 | | |
|---|---|---|---|
| | ESTIMATED VALUE (nm) | ABSOLUTE VALUE OF DIFFERENCE (nm) | ACCURACY (%) |
| Thyroglobulin | 8.5 | 0.1 | 99.4 |
| β-Amylase | 5.2 | 0.2 | 95.8 |
| BSA | 4.2 | 0.7 | 79.3 |
| Carbonic anhydrase | 1.7 | 0.4 | 83.2 |
| Lysozyme | 2.0 | 0.1 | 95.8 |
| Aprotinin | 1.2 | 0.2 | 88.0 |

FIG. 10D

| | COMPARATIVE EXAMPLE 2 | | |
|---|---|---|---|
| | ESTIMATED VALUE (nm) | ABSOLUTE VALUE OF DIFFERENCE (nm) | ACCURACY (%) |
| Thyroglobulin | 7.5 | 1.1 | 86.7 |
| β-Amylase | 4.4 | 1.0 | 80.9 |
| BSA | 3.5 | 0.0 | 100.0 |
| Carbonic anhydrase | 1.2 | 0.9 | 58.7 |
| Lysozyme | 1.4 | 0.5 | 76.1 |
| Aprotinin | 0.8 | 0.6 | 54.3 |

|  | DIFFUSION TIME MEASURED VALUE (μs) | THEORETICAL VALUE OF HYDRODYNAMIC RADIUS (nm) |
| --- | --- | --- |
| Thyroglobulin | 350 | 8.6 |
| β-Amylase | 240 | 5.4 |
| BSA | 191 | 3.5 |
| Carbonic anhydrase | 137 | 2.1 |
| Lysozyme | 117 | 1.9 |
| Aprotinin | 87 | 1.4 |
| Alexa 647 DYE | 49 | 0.8 |

FIG. 12A

EXAMPLE 5

| | ESTIMATED VALUE (nm) | ABSOLUTE VALUE OF DIFFERENCE (nm) | ACCURACY (%) |
|---|---|---|---|
| Thyroglobulin | 8.5 | 0.1 | 98.7 |
| β-Amylase | 5.3 | 0.1 | 98.8 |
| BSA | 3.9 | 0.4 | 87.7 |
| Carbonic anhydrase | 2.4 | 0.3 | 86.5 |
| Lysozyme | 1.8 | 0.1 | 95.3 |
| Aprotinin | 1.0 | 0.4 | 67.9 |
| Alexa 647 DYE | -0.1 | 0.9 | -17.3 |

FIG. 12B

| REFERENCE EXAMPLE | | |
|---|---|---|
| ESTIMATED VALUE (nm) | ABSOLUTE VALUE OF DIFFERENCE (nm) | ACCURACY (%) |
| Thyroglobulin | 3.9 | 4.7 | 45.2 |
| β-Amylase | 3.0 | 2.4 | 55.8 |
| BSA | 2.6 | 0.9 | 75.1 |
| Carbonic anhydrase | 2.2 | 0.1 | 95.3 |
| Lysozyme | 2.0 | 0.1 | 92.6 |
| Aprotinin | 1.8 | 0.4 | 71.3 |
| Alexa 647 DYE | 1.5 | 0.7 | 12.5 |

FIG. 12C

| COMPARATIVE EXAMPLE 3 | ESTIMATED VALUE (nm) | ABSOLUTE VALUE OF DIFFERENCE (nm) | ACCURACY (%) |
|---|---|---|---|
| Thyroglobulin | 5.7 | 2.9 | 66.4 |
| β-Amylase | 3.9 | 1.5 | 72.6 |
| BSA | 3.1 | 0.4 | 89.1 |
| Carbonic anhydrase | 2.2 | 0.1 | 93.5 |
| Lysozyme | 1.9 | 0.0 | 99.5 |
| Aprotinin | 1.4 | 0.0 | 98.5 |
| Alexa 647 DYE | 0.8 | 0.0 | 100.0 |

β-Amylase (5.4nm)

Thyroglobulin (8.6nm)

METHOD FOR ACQUIRING INFORMATION OF TARGET POLYPEPTIDE AND REAGENT KIT

CROSS REFERENCE TO RELATED APPLICATIONS

This application claims priority from prior Japanese Patent Application No. 2020-079588 filed on Apr. 28, 2020, entitled "Method for acquiring information of target polypeptide and reagent kit", the entire contents of which are incorporated herein by reference.

FIELD OF THE INVENTION

The present invention relates to a method for acquiring information of a target polypeptide and a reagent kit.

BACKGROUND

Fluorescence correlation spectroscopy (FCS) and fluorescence cross-correlation spectroscopy (FCCS) are known as analytical methods for acquiring information on the size of a polypeptide. Eilon Sherman, Biophysical Journal Volume 94, June 2008, 4819-4827, "Using Fluorescence Correlation Spectroscopy to Study Conformational Changes in Denatured Proteins" describes structural changes due to protein inactivation using FCS. This document describes that size of a specimen protein is estimated by proportional calculation using a diffusion time obtained by FCS for a dye and a specimen protein with a known diffusion coefficient. Tingjuan Gao, PROTEIN SCIENCE 2011 VOL 20: 437-447, "Characterizing diffusion dynamics of a membrane protein associated with nanolipoproteins using fluorescence correlation spectroscopy" describes that a diffusion time of polystyrene beads of each size is determined by fluorescence correlation spectroscopy, using standard samples containing dye-labeled polystyrene beads of different sizes and the like, and a calibration curve is prepared. This document describes that size of a target protein is calculated by applying the diffusion time determined by FCS for the target protein to the calibration curve.

The present inventors have found that a conventional method has a large measurement error and has a problem in terms of accuracy.

An object of the present invention is to provide a method for more accurately acquiring information on size of a target polypeptide and a reagent kit.

SUMMARY OF THE INVENTION

The scope of the present invention is defined solely by the appended claims and is not affected to any degree by the statements within this summary.

One embodiment of the present invention relates to a method for acquiring information of a target polypeptide. The method for acquiring information of a target polypeptide includes acquiring a diffusion time of a fluorescently labeled target polypeptide and a diffusion time of each of a plurality of fluorescently labeled reference polypeptides by fluorescence correlation spectroscopy or fluorescence cross-correlation spectroscopy; and acquiring information on size of the fluorescently labeled target polypeptide from the diffusion time of the fluorescently labeled target polypeptide with reference to the diffusion times of the plurality of fluorescently labeled reference polypeptides. Information on size of each of the plurality of fluorescently labeled reference polypeptides is known, and the sizes of the plurality of reference polypeptides are different from each other.

According to the method for acquiring information of a protein of the present embodiment, the information on size of the target polypeptide can be acquired more accurately as compared with Non-Patent Document 1 and Non-Patent Document 2.

One embodiment of the present invention relates to a reagent kit.

One embodiment of the reagent kit relates to a reagent kit including a plurality of fluorescently labeled reference polypeptides. Information on size of each of the plurality of fluorescently labeled reference polypeptides is known, and the sizes of the plurality of reference polypeptides are different from each other. The reagent kit is used as the method for acquiring information about a protein.

Another embodiment of the reagent kit relates to a reagent kit including a plurality of reference polypeptides and a fluorescently labeled antibody that binds to each of the plurality of reference polypeptides. Information on size of each of the plurality of fluorescently labeled reference polypeptides is known, and the sizes of the plurality of reference polypeptides are different from each other. The reagent kit is used for the method for acquiring information on a target polypeptide.

According to the reagent kit of the above embodiment, the information on size of the target polypeptide can be acquired more accurately as compared with Non-Patent Document 1 and Non-Patent Document 2.

BRIEF DESCRIPTION OF THE DRAWINGS

In FIG. 4C, abbreviations indicate AP: aprotinin, L: lysozyme, CA: carbonic anhydrase, BS: bovine serum albumin, BA: β-amylase. AF: apoferritin, and T: thyroglobulin, respectively. An error bar shows a standard deviation of three measurements.

FIG. 10C shows the estimated value of size (nm), the absolute values of difference in size between predicted values and theoretical values (nm) and the percentage accuracy obtained in Example 4. FIG. 10D shows the estimated value of size (nm), the absolute values of difference in size between predicted values and theoretical values (nm) and the percentage accuracy obtained in Comparative Example 2.

FIG. 12A shows the result of Example 5, FIG. 12B shows the result of Reference Example, and FIG. 12C shows the result of Comparative Example 3.

DETAILED DESCRIPTION OF THE PREFERRED EMBODIMENTS

Figure 1:
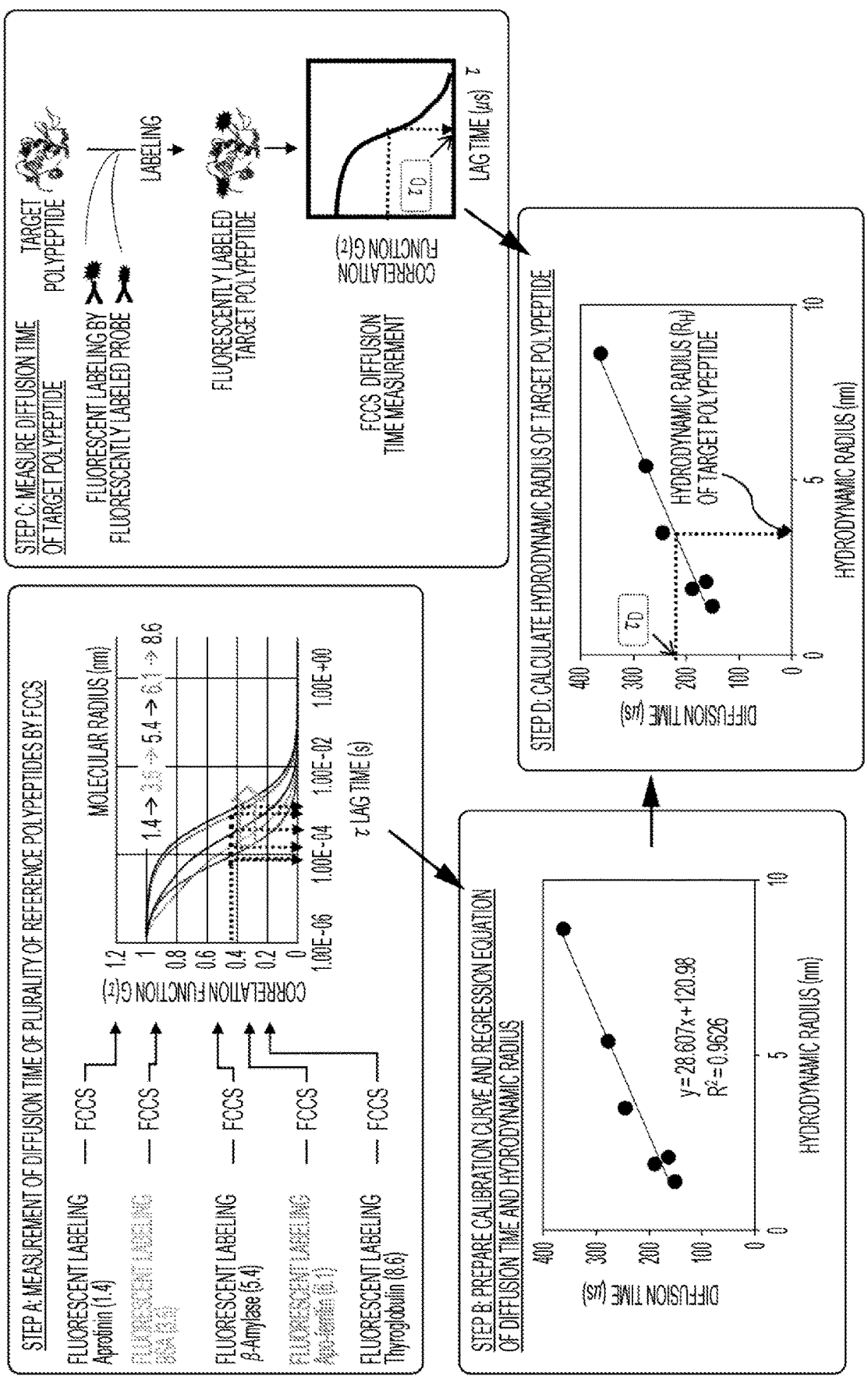
FIG. 1 shows an outline of the present invention. This outline is an example using FCCS.

1. Method for Acquiring Information of Target Polypeptide 1-1. Explanation of Terms A reference polypeptide is a polypeptide used as a reference for acquiring information on the size of a target polypeptide, and size information of reference polypeptide is known. It is preferable to use a plurality of reference polypeptides having different sizes. For example, 2, 3, 4, 5, 6 or 7 types of reference polypeptides can be used.

The size of the reference polypeptide is appropriately selected depending on the expected size of the target polypeptide. For example, the reference polypeptide has a hydrodynamic radius of 1 nm or more and 20 nm or less. The plurality of reference polypeptides includes at least a first reference polypeptide and a second reference polypeptide. The first reference polypeptide and the second reference polypeptide are different in size from each other. In one embodiment, a hydrodynamic radius of the first reference polypeptide is at least twice the hydrodynamic radius of the second reference polypeptide. In another embodiment, the first reference polypeptide has a hydrodynamic radius of 1 nm or more and less than 5 nm, and the second reference polypeptide has a hydrodynamic radius of 5 nm or more and 10 nm or less.

The plurality of reference polypeptides may include the first reference polypeptide, the second reference polypeptide and a third reference polypeptide. The first reference polypeptide, the second reference polypeptide, and the third reference polypeptide have different sizes. In one embodiment, the first reference polypeptide has a hydrodynamic radius of 1 nm or more and less than 3 nm, the second reference polypeptide has a hydrodynamic radius of 3 nm or more and less than 6 nm, and the third reference polypeptide has a hydrodynamic radius of 6 nm or more and less than 9 nm.

As the reference polypeptide, specifically, Aprotinin (hydrodynamic radius 1.4 nm); Hen egg-white lysozyme (lysozyme) (hydrodynamic radius 1.9 nm); Carbonic anhydrase (CA) (hydrodynamic radius 2.1 nm), bovine serum albumin (BSA) (hydrodynamic radius 3.5 nm): β-amylase (hydrodynamic radius 5.4 nm), Apo-ferritin (hydrodynamic radius 6.4 nm), Thyroglobulin (hydrodynamic radius 8.6 nm) or the like can be used. From these, two or more can be selected depending on the expected size of the target polypeptide.

The target polypeptide is a polypeptide to be measured. The target polypeptide may be a polypeptide derived from a specimen collected from a living body. Examples of the specimen include whole blood, plasma, serum, cerebrospinal fluid, urine and the like. The target polypeptide can be a protein, a fragment of a protein, or an aggregate of polypeptides. The aggregate of polypeptides also called a "polymer" or a "multimer," is formed by physical and/or chemical polymerization of a plurality of monomer molecules. Specific examples of the aggregate include von Willebrand factor aggregates, amyloid β aggregates, tau protein aggregates, serum-amyloid-A-protein aggregates, IgG-light chain aggregates, AApoAI aggregates, AApoAII aggregates, ATTR aggregates, DISC1 aggregates, FUS aggregates, IAPP aggregates, SOD1 aggregates, α-synuclein aggregates, TDP-43 aggregates, huntingtin aggregates, lysozyme aggregates, and the like. The aggregate of polypeptides can be used to determine the presence or absence of disease. For example, a von Willebrand factor exists as an aggregate (von Willebrand factor multimer) in the blood of healthy people, but this aggregate may be decomposed in acquired von Willebrand factor syndrome. That is, information on the size of von Willebrand factor can be an index of acquired von Willebrand factor syndrome. Information on the size of amyloid β aggregates, tau protein aggregates or the like can be an index of neurological diseases such as Alzheimer's disease.

Fluorescence correlation spectroscopy (hereinafter sometimes referred to as "FCS") is a method for detecting a one-color fluorescent dye bound to one molecule. Fluorescence cross-correlation spectroscopy (hereinafter sometimes referred to as "FCCS") is a method for detecting two-color fluorescent dyes bound to one molecule. Devices that perform FCS or FCCS analysis are known. For example, it is possible to analyze both FCS and FCCS by combining the inverted microscope Zeiss Axio Observer (Carl Zeiss Co., Ltd.) and Zen software of the same company. Examples of the FCS analyzer include a fluorescence correlation spectrometer FCS compact series (Hamamatsu Photonics K. K.). Examples of the FCCS analyzer include a fluorescence cross-correlation spectrometer FCCS compact (Hamamatsu Photonics K.K.).

Diffusion time is generally represented by the symbol m or the like. For example, diffusion time can be expressed in units such as microseconds (μs) or milliseconds (ms).

Examples of the information on size acquired by FCS or FCCS include a hydrodynamic radius, a hydrodynamic diameter, a volume, and the like. The hydrodynamic radius and hydrodynamic diameter can be expressed in units such as nanometers (nm). The volume can be expressed in units such as cubic nanometers (nm$^3$).

Since the fluorescent dye used in FCS is one color, any fluorescent dye within a range that can be detected by the FCS analyzer can be used.

FCCS, on the other hand, uses two types of fluorescent dyes and detects these fluorescent dyes almost simultaneously. Therefore, it is preferable that fluorescence wavelengths of the two types of fluorescent dyes used are different from each other. For example, when a peak of the fluorescence wavelength of one of the two-color fluorescent dyes is in a range of 400 nm to 550 nm, a peak of the fluorescence wavelength of the other fluorescent dye is preferably in a range of 600 nm to 800 nm. Expressed in terms of excitation wavelength, when a peak of the excitation wavelength of one of the two-color fluorescent dyes is in a range of 400 nm to 500 nm, a peak of the excitation wavelength of the other fluorescent dye is preferably in a range of 530 nm to 700 nm. For example, when Alexa Fluor (trademark) 488, FITC, Cy3, Cy2 or the like is used for one fluorescent dye, Alexa Fluor (trademark) 647, Rhodamine, Cy5 or the like can be used for the other fluorescent dye. When two types of fluorescent dyes having overlapping fluorescence spectra are used, a fluorescence signal may be detected through, for example, a bandpass filter or the like.

It is preferable that a fluorescent dye labeled on the target polypeptide and a fluorescent dye labeled on the reference polypeptide are the same.

The reference polypeptide or target polypeptide can be labeled with a fluorescent dye via a chemical bond such as a covalent bond by a known method. Hereinafter, a fluorescent labeling method via a chemical bond is also referred to as a direct labeling method. For example, a fluorescent dye can be labeled on a polypeptide by a covalent bond using amino labeling, thiol labeling, or the like. Amino labeling can label a fluorescent dye, using N-hydroxysuccinimide (NHS) ester, sulfodicholorphenol (SDP) ester, tetrafluorophenyl (TFP) ester, etc. of the fluorescent dye, by an amine coupling reaction between the ester and an amine of the polypeptide. Thiol labeling can label a fluorescent dye by a covalent bond between a maleimide derivative of the fluorescent dye and a thiol group of the polypeptide.

Upon labeling, the polypeptide and the fluorescent dye ester or fluorescent dye derivative are mixed in a predetermined reaction buffer. A mixing ratio of the polypeptide to the fluorescent dye ester or fluorescent dye derivative can be 2 mol to 50 mol of the fluorescent dye ester or fluorescent dye derivative to 1 mol of the polypeptide. When two fluorescent dyes are used, for example, the mixing ratio can be 2 mol to 50 mol of the first fluorescent dye ester or first fluorescent dye derivative and 2 mol to 50 mol of the second fluorescent dye ester or second fluorescent dye derivative, to 1 mol of the polypeptide. It is preferable to mix the first and second fluorescent dye esters or fluorescent dye derivatives so that they have the same molar ratio.

A labeling reaction can be performed in the dark, for example, at 20° C. to 28° C. for about 30 minutes to 2 hours with stirring.

The fluorescently labeled polypeptide can be purified by desalting the reaction solution using a desalting/buffer exchange column or the like to remove the unreacted fluorescent dye ester or fluorescent dye derivative. As the desalting/buffer exchange column, for example, HiTrap Desalting (GE Healthcare Cat. No. 29048684) can be used.

In another embodiment, a fluorescently labeled probe can be used on the reference polypeptide or target polypeptide, so that the fluorescent dye can be labeled via a probe by a known method. Hereinafter, a fluorescent labeling method via a probe is also referred to as an indirect labeling method. The probe is not limited as long as it can specifically bind to an individual reference polypeptide, target polypeptide or the like. As used herein, specifically binding means that it may include a non-specific reaction to an extent that it does not adversely affect the measurement. Examples of the probe include antibodies, lectins, aptamers, and the like. The probe is preferably an antibody. As the antibody, any of a polyclonal antibody, a monoclonal antibody, and a fragment thereof (for example, Fab, F(ab'), F(ab)$_2$, or the like) can be used. Also, immunoglobulin classes and subclasses are not particularly limited. The antibody may be screened from an antibody library, and may be a chimeric antibody, scFv, a single domain antibody (sdAb), or the like. Examples of the antibody may include VHH (variable domains of heavy chain of heavy chain antibody) domain of camelid-derived heavy chain antibody, VNAR (variable new antigen receptor) domains derived from cartilaginous fish (for example, shark) heavy chain antibody IgNAR (new antigen receptor), and the like. As the antibody used as the fluorescently labeled probe, it is preferable to use Fab, VHH, VNAR or scFv with a small molecular size of itself.

In FCS, a probe that binds to an individual reference polypeptide, or target polypeptide, can be labeled with a fluorescent dye of the same fluorescence wavelength, preferably the same fluorescent dye.

In FCCS, the two types of fluorescent dyes with different fluorescence wavelengths described in 1-1. above can be bound to a polypeptide to perform fluorescent labeling so that a reference polypeptide contains the two types of fluorescent dyes. In this case, it is preferable to bind a first probe containing one of the two types of fluorescent dyes and a second probe containing the other fluorescent dye to the polypeptide. Similarly, also for the target polypeptide, the two types of fluorescent dyes with different fluorescence wavelengths can be bound to two different probes to perform fluorescence labeling so that the target polypeptide contains the two types of fluorescent dyes. At this time, it is preferable that the two types of fluorescent dyes labeled on the reference polypeptide are the same as the fluorescent dyes labeled on the target polypeptide.

Regions within the polypeptide recognized by the first and second probes may be different or the same, but preferably different. When the probe is an antibody, an epitope of a first antibody containing a first fluorescent dye and an epitope of a second antibody containing a second fluorescent dye are preferably different sites within one polypeptide.

The fluorescently labeled probe can be mixed and bound to an individual reference polypeptide or target polypeptide, in a buffer such as PBS, in a specimen, or in a diluted specimen. The diluted specimen may be a specimen diluted about 1.5 to 10 times with PBS, physiological saline or the like. The reaction time is, for example, at room temperature (about 23° C. to 27° C.), for about 3 to 7 minutes. The fluorescently labeled antibody can be added, for example, at a protein concentration of about 50 nM to 150 nM. By this reaction, each fluorescently labeled reference polypeptide or a fluorescently labeled target polypeptide can be prepared.

1-2. Method for Acquiring Information of Target Polypeptide

One embodiment relates to a method for acquiring information of a target polypeptide (hereinafter, may be simply referred to as an "information acquisition method"). The information acquisition method includes a first step of acquiring a diffusion time of a fluorescently labeled target polypeptide and diffusion times of a plurality of fluorescently labeled reference polypeptides by FCS or FCCS, and a second step of acquiring information on size of the fluorescently labeled target polypeptide based on the diffusion times of the plurality of fluorescently labeled reference polypeptides.

(1) First Step: Diffusion Time Acquiring

In the first step, the diffusion times of the fluorescently labeled reference polypeptides are acquired from each of standard samples. The standard samples can be prepared using reference polypeptides fluorescently labeled with direct labeling or reference polypeptides fluorescently labeled with indirect labeling. The standard samples include a first standard sample containing a fluorescently labeled first reference polypeptide and a second standard sample containing a fluorescently labeled second reference polypeptide. Therefore, the diffusion time acquired from each of standard samples includes a diffusion time of the fluorescently labeled first reference polypeptide and a diffusion time of the fluorescently labeled second reference polypeptide. When the standard sample further includes a third standard sample containing a fluorescently labeled third reference polypeptide, the diffusion time acquired from the standard sample includes at least the diffusion time of the fluorescently labeled first reference polypeptide, the diffusion time of the fluorescently labeled second reference polypeptide, and a diffusion time of the fluorescently labeled third reference polypeptide.

When each reference polypeptide is fluorescently labeled by the direct labeling method, in one embodiment, the reference polypeptide is reacted with the fluorescent dye in an aqueous solvent, and the reaction solution can be used as a standard sample. In another embodiment, the fluorescently labeled reference polypeptide is mixed with an aqueous solvent, and the mixture liquid can be used as a standard sample. The standard sample is prepared for each reference polypeptide. The "aqueous solvent" in the present specification is not particularly limited as long as it is a liquid solvent. Examples of the aqueous solvent include water, a buffer solution, physiological saline, and the like. A liquid specimen collected from a living body may be used as an 'aqueous solvent'. The specimen may contain an insoluble component such as cells, and examples thereof include whole blood, plasma, serum, cerebrospinal fluid, urine, and the like. If necessary, the specimen may be subjected to pretreatment such as removal of insoluble components or dilution by a known method.

When the reference polypeptide is fluorescently labeled by the indirect labeling method, in one embodiment, the reference polypeptide is reacted with the fluorescent probe in an aqueous solvent. In this embodiment, the reaction solution can be used as a standard sample. In another embodiment, the fluorescently labeled reference polypeptide is mixed with an aqueous solvent, and the mixture liquid can be used as a standard sample.

In the first step, the diffusion time of the fluorescently labeled target polypeptide is acquired from a measurement sample.

The measurement sample can be prepared using the target polypeptide fluorescently labeled by the direct labeling method or the target polypeptide fluorescently labeled by the indirect labeling method. When the target polypeptide is fluorescently labeled by the direct labeling method, in one embodiment, the target polypeptide is reacted with the fluorescent dye in an aqueous solvent, and the reaction solution can be used as a measurement sample.

When the target polypeptide is fluorescently labeled by the indirect labeling method, in one embodiment, the target polypeptide is reacted with the fluorescent probe in an aqueous solvent. In this embodiment, the reaction solution can be used as a measurement sample. In another embodiment, the fluorescently labeled target polypeptide is mixed with an aqueous solvent, and the mixture liquid can be used as a measurement sample.

A diffusion time of molecules in the solution is affected by viscosity of the aqueous solvent. Therefore, preferably, the viscosity of an aqueous solvent containing the fluorescently labeled reference polypeptide is about the same as the viscosity of an aqueous solvent containing the fluorescently labeled target polypeptide. More preferably, the aqueous solvent containing the fluorescently labeled reference polypeptide and the aqueous solvent containing the fluorescently labeled target polypeptide are the same. When the fluorescently labeled target polypeptide in the measurement sample is contained in an aqueous solvent containing impurities such as a specimen collected from a living body, the standard sample is preferably prepared by mixing each fluorescently labeled reference polypeptide with the same aqueous solvent as the aqueous solvent used in the measurement sample. In this case, in a more preferred embodiment, an aqueous solvent such as a specimen collected from a living body is divided into a plurality of parts, one of which is added with a fluorescently labeled probe that labels the target polypeptide, and the other of which is added with a fluorescently labeled reference polypeptide. This may prepare a measurement sample containing the fluorescently labeled target polypeptide and a standard sample containing the fluorescently labeled reference polypeptide. More specifically, a specimen containing a target polypeptide collected from a living body is divided into a first aliquot, a second aliquot and a third aliquot. By mixing the first aliquot with a fluorescently labeled probe that binds to the target polypeptide, a measurement sample containing the fluorescently labeled target polypeptide can be prepared. A first standard sample can be prepared by mixing the second aliquot with the fluorescently labeled first reference polypeptide. A second standard sample can be prepared by mixing the third aliquot with the fluorescently labeled second reference polypeptide.

The measurement sample containing each fluorescently labeled reference polypeptide or fluorescently labeled target polypeptide has a viscosity of preferably about 0.800 to 30.00 mPa·s at 23° C. The amount of the fluorescent dye contained in the peptide solution is preferably adjusted to be about 0.1 nM to 1000 nM.

In one embodiment, a binding mode between the target polypeptide and the fluorescent dye is the same as a binding mode between the reference poly peptide and the fluorescent dye. For example, when the fluorescent dye binds to the target polypeptide by direct labeling, the fluorescent dye may bind to the reference polypeptide by direct labeling. When the fluorescent dye binds to the target polypeptide by indirect labeling, the fluorescent dye may bind to the reference polypeptide by indirect labeling. In this case, the type of fluorescently labeled probe used for indirect labeling of the target polypeptide and the fluorescent dye is preferably the same as the type of the fluorescently labeled probe used for indirect labeling of the reference polypeptide and the fluorescent dye. As a specific example, the target polypeptide is labeled with a fluorescently labeled antibody that specifically binds to the target polypeptide, and the reference polypeptide is labeled with a fluorescently labeled antibody that specifically binds to the reference polypeptide.

In another embodiment, the binding mode between the target polypeptide and the fluorescent dye differs from the binding mode between the reference polypeptide and the fluorescent dye. The binding modes are not necessarily the same since the reference polypeptide is only required to be able to serve as a reference to the target polypeptide for information on size of the polypeptide. For example, when the fluorescent dye binds to the target polypeptide by direct labeling, the fluorescent dye may bind to the reference polypeptide by indirect labeling. When the fluorescent dye binds to the target polypeptide by indirect labeling, the fluorescent dye may bind to the reference polypeptide by direct labeling. As a specific example, the target polypeptide is labeled with a fluorescently labeled antibody that specifically binds to the target polypeptide, and the reference polypeptide is labeled with a fluorescent dye via a covalent bond.

In the acquisition of the diffusion time described later, a diffusion time of the fluorescently labeled target polypeptide in the measurement sample, a diffusion time of the fluorescently labeled first reference polypeptide in the first standard sample, and a diffusion time of the fluorescently labeled second reference polypeptide in the second standard sample can be acquired, respectively.

For example, about 30 µl of each sample is independently dispensed into a 384-well glass bottom plate (Sigma-Aldrich. M4437-16EA) or the like and used for measurement. Temperature at the time of measurement of the standard sample and the measurement sample is preferably about the same, and more preferably about 23° C. to 25° C. for example.

A laser used for the measurement is not limited as long as it can excite the fluorescent dye contained in each sample. The laser focuses to about 1 fL region and detects a fluorescence signal emitted when the fluorescently labeled polypeptide in the sample passes through a confocal region. In FCS, a single laser is used to excite a fluorescent dye to acquire a fluorescence signal over time. In FCCS two lasers are used to excite a fluorescent dye to acquire a fluorescence signal over time. Raw data of the detected fluorescence signal is a data group represented by signal intensity and measurement time. Since processing of this raw data differs between FCS and FCCS, both will be described separately below.

The raw data may be preprocessed to remove a measured value that indicates baseline drift or burst (average fluorescence brightness and over three times higher fluorescence signal) as required.

(i) FCS

The FCS analyzer described above acquires raw data for measurement of single-wavelength photon. Autocorrelation analysis of the raw data is performed to acquire a raw curve of autocorrelation function. Fitting by an appropriate fitting model is performed on the curve of autocorrelation function, and a correlation curve drawn by correlation functions $G(\tau)$ and lag time ($\tau$) is obtained.

When the measurement sample and the standard sample are prepared using a specimen collected from a living body, the fitting by the autocorrelation function can be performed with a two-component model. A first component used in the two-component model can be, for example, an unreacted fluorescently labeled probe. A second component can be each complex of each polypeptide and its corresponding fluorescently labeled probe. For example, a one-component model is selected on analysis software such as Zen software, and a diffusion time of the first component is measured for each fluorescently labeled probe. Next, a two-component model is selected on the same software, a diffusion time of the first component is fixed to the diffusion time of the first component measured earlier, and a diffusion time of the second component is measured.

(ii) FCCS

The FCCS analyzer described above acquires raw data for measurement of two-wavelength photon. Cross-correlation analysis of the raw data is performed to acquire a raw curve of cross-correlation function. Fitting is performed on the curve of cross-correlation function with an appropriate fitting model, and for example, a correlation curve represented by lag time ($\tau$) on an X-axis and cross-correlation function $G(\tau)$ on a Y-axis is obtained. Specific functions are shown in Eq. 1A, Eq. 1B, Eq. 2, and Eq. 3 of Examples.

In FCCS, the fitting of the correlation function can be performed with a one-component model. One component is each complex of each polypeptide and its corresponding fluorescently labeled probe. A one-component model is selected on software such as Zen software, and a diffusion time of each complex is measured. Since FCCS uses two types of fluorescent dyes for one polypeptide, more accurate analysis is possible.

A value of $G(\tau)$ when $\tau$ is 0 is taken as a value of the origin, and the diffusion time indicates lag time $\tau$ at half the value of the origin, i.e, half of $G(0)$. Specifically, if the $G(\tau)$ value where lag time ($\tau$) is 0 is a, the diffusion time is the lag time $\tau$ where $G(\tau)$ is $a \times \frac{1}{2}$. More specifically, in the correlation function $G(\tau)$, when the value at $G(0)$ is converted to 1, the diffusion time is lag time $\tau$ where $G(\tau)$ is 0.5. Therefore, the correlation function $G(\tau)$ may be standardized so that the maximum value is "1" and the minimum value is "0". When the correlation function $G(\tau)$ is standardized, a combination of the maximum value and the minimum value can be set as appropriate. For example, it may be a combination in which the maximum value is "2" and the minimum value is "1", or a combination in which the maximum value is "100" and the minimum value is "0".

(2) Second Step: Information Acquiring

Information on size of the target polypeptide can be acquired from the diffusion time of the target polypeptide with reference to the diffusion time corresponding to a predetermined $G(\tau)$ value of the reference polypeptide contained in each of standard samples obtained in the first step. When the diffusion time of the fluorescently labeled first reference polypeptide and the diffusion time of the fluorescently labeled second reference polypeptide have been acquired, the information on size of the target polypeptide is acquired with reference to these diffusion times. When the diffusion time of the fluorescently labeled first reference polypeptide, the diffusion time of the fluorescently labeled second reference polypeptide and the diffusion time of the fluorescently labeled third reference polypeptide have been acquired, the information on size of the target polypeptide is acquired with reference to these diffusion times.

Preferably, a regression equation is obtained based on the diffusion time corresponding to a predetermined $G(\tau)$ value of the reference polypeptide contained in each of standard samples and the size of each reference polypeptide known in advance, and a calibration curve is prepared. The diffusion time corresponding to the $G(\tau)$ value of the same target polypeptide as the predetermined $G(\tau)$ value of the reference polypeptide is acquired. The acquired diffusion time of the target polypeptide is applied to the calibration curve to acquire the information on size of the target polypeptide.

The size of the target polypeptide obtained here is the size of the target polypeptide that is not fluorescently labeled.

(3) Example of Embodiment

A principle of a method of the present embodiment will be described with reference to a specific example shown in FIG. 1. The example shown in FIG. 1 is merely an example, and the present disclosure is not construed as being limited to this example. FIG. 1 shows an information acquisition method using fluorescence cross-correlation spectroscopy.

Diffusion time (also referred to as lag time) τ is acquired by FCCS for a plurality of reference polypeptides labeled with a fluorescent dye in Step A. Molecules in a solution are always moving freely due to Brownian motion or the like. FCS and FCCS use a confocal laser to detect a fluorescence signal emitted when molecules in the solution pass through a confocal region. Raw data of the detected fluorescence signal is represented by signal intensity and measurement time. In FCCS, this is fitted by a cross-correlation function, and for example, a correlation curve represented by diffusion time (τ) on an X-axis and correlation function G(τ) on a Y-axis is obtained. In the case of FCS, the raw data of the detected fluorescence signal is fitted with an autocorrelation function, and a curve of the correlation function G(τ) can be obtained. The correlation function G(τ) shown in Step A is a correlation curve after standardization.

In Step B, a calibration curve is prepared. Since the size of the reference polypeptide is known in advance, a regression equation is obtained from a diffusion time corresponding to a constant G(τ) value in each reference polypeptide and the size of each reference polypeptide (here, the hydrodynamic radius), and a calibration curve can be prepared.

Step C is a step of obtaining the diffusion time of the fluorescently labeled target polypeptide. The diffusion time can be obtained in the same manner as the diffusion time of the reference polypeptide.

Steps A and C correspond to the acquiring the diffusion time of the fluorescently labeled target polypeptide and the diffusion times of the plurality of fluorescently labeled reference polypeptides. The order of Step A and Step C is not limited. Step A may be performed before Step C. Step C may be performed before Step A, or Step A and Step C may be performed at the same time.

Step D is a step of acquiring information on size of the target polypeptide from the calibration curve prepared in Step B and the diffusion time of the target polypeptide obtained in Step C. The diffusion time of the target polypeptide corresponding to the G(i) value at the time of preparing the calibration curve is applied to the calibration curve to acquire information on molecular size of the target polypeptide.

2. Reagent Kit

Figure 2:
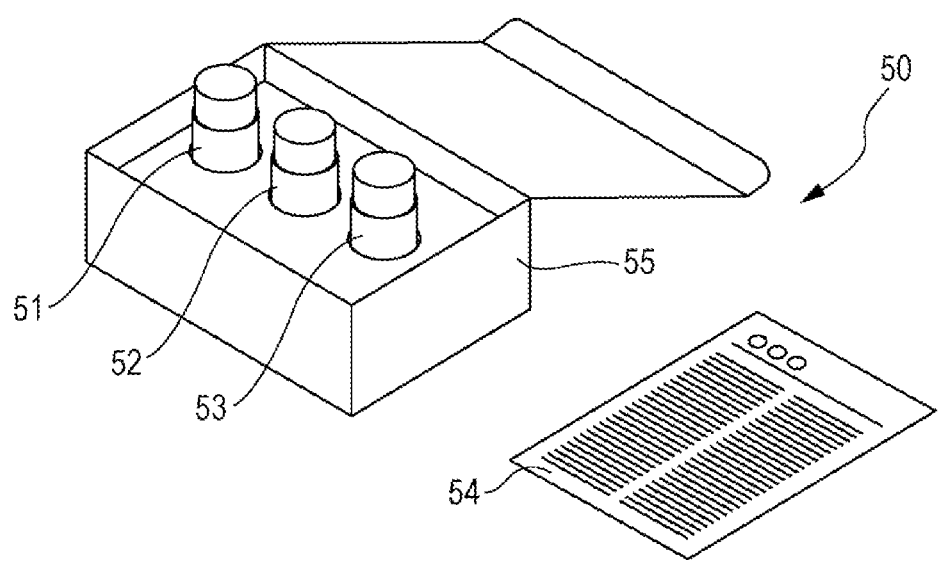
FIG. 2 shows an appearance of a reagent kit.

One embodiment relates to a reagent kit. The reagent kit contains the plurality of fluorescently labeled reference polypeptides described in 1-2. above. This reagent kit can be used as a calibrator to acquire information on size of the target polypeptide. It is preferred that the plurality of fluorescently labeled reference polypeptides is respectively contained in separate containers. The reagent kit can be provided to a user as a kit shown in FIG. 2. A reagent kit 50 includes an outer box 55, a first container 51 containing a fluorescently labeled first reference polypeptide, a second container 52 containing a fluorescently labeled second reference polypeptide, a third container 53 containing a fluorescently labeled third reference polypeptide, and an attached document 54 of the reagent kit. In the attached document 54, a handling method of the reagent kit, storage conditions, expiration date, etc. can be described. A container containing an aqueous solvent for dilution or the like may be included in the outer box 55.

The reagent kit may be provided to the user as a reagent kit including a plurality of reference polypeptides and a fluorescently labeled antibody that binds to each of the plurality of reference polypeptides.

The fluorescently labeled antibody that binds to each of the plurality of reference polypeptides may include a first fluorescently labeled antibody and a second fluorescently labeled antibody that bind to one reference polypeptide. Preferably, a fluorescence wavelength of a labeled fluorescent dye of the first fluorescently labeled antibody is different from a fluorescence wavelength of a fluorescent dye labeled with the second fluorescently labeled antibody. An epitope of the first fluorescently labeled antibody is preferably different from an epitope of the second fluorescently labeled antibody.

EXAMPLES

The present disclosure will be described in more detail below with reference to examples. However, the present disclosure is not construed as limited to the examples.

I. Method

1. Reference Polypeptides

As reference polypeptides, Aprotinin (Sigma-Aldrich, A3886-1VL, hydrodynamic radius 1.4 nm): Hen egg-white lysozyme (lysozyme) (Sigma-Aldrich, L4919-500 MG, hydrodynamic radius 1.9 nm); Carbonic anhydrase (CA) (Sigma-Aldrich, C7025-1VL, hydrodynamic radius 2.1 nm): bovine serum albumin (BSA) (Sigma-Aldrich, A8531-1VL, hydrodynamic radius 3.5 nm): β-amylase (Sigma-Aldrich, A8781-1VL, hydrodynamic radius 5.4 nm), Apo-ferritin (Sigma-Aldrich, A3660-1VL, hydrodynamic radius 6.4 nm), Thyroglobulin (Sigma-Aldrich, T1001-100 MG, hydrodynamic radius 8.6 nm) were used.

2. Fluorescent Labeling on Polypeptides (1) Direct Labeling of Fluorescent Dyes on Polypeptides Amines of the reference polypeptides and target polypeptide were labeled with a fluorescent dye by an amine coupling reaction, using an N-hydroxy succinimidyl (NHS) ester of Alexa Fluor (trademark) 647 (Invitrogen, Cat. No. A20006) and/or Alexa Fluor (trademark) 488 (Invitrogen, Cat. No. A20000). Each polypeptide measured by FCS was labeled with one type of the above fluorescent dyes. Each polypeptide measured by FCCS was labeled with two types of the above fluorescent dyes.

The amine coupling reaction was performed by mixing the fluorescent dye and the polypeptide in PBS with stirring at 400 rpm at room temperature in the dark for 1 hour.

In FCS, a mixing ratio of the polypeptide and the NHS ester of the fluorescent dye was set to, by molar ratio, Aprotinin:fluorescent dye=1:2, CA:fluorescent dye=1:2, lysozyme:fluorescent dye=1:2, BSA:fluorescent dye=1:5, β-amylase:fluorescent dye=1:20, Apo-ferritin:fluorescent dye=1:20, and Thyroglobulin:fluorescent dye=1:50. When using two fluorescent dyes in FCCS, first and second fluorescent dyes were mixed so that their molar ratios were the same, for example, a molar ratio of Aprotinin:first fluorescent dye:second fluorescent dye=1:2:2.

After the amine coupling reaction, the reaction solution was desalted using a HiTrap Desalting column (GE Healthcare Cat. No. 29048684) to remove the unreacted fluorescent dye. The desalted reaction solution was further subjected to Ultra High Performance Liquid Chromatography (UHPLC) using a TSKgel G3000SWXL column (TOSOH Cat. No. 08541) to analyze quality of the fluorescently labeled polypeptide.

The quality of the fluorescently labeled polypeptide was evaluated by acquiring fluorescence spectra in a 230 nm to 70) nm region and observing a 280 nm region derived from protein and a peak in a fluorescence wavelength region of each fluorescent dye.

(2) Indirect Labeling of Fluorescent Dyes on Polypeptides

Indirect labeling was used in a measurement to detect a target polypeptide in a specimen containing multiple components such as serum and plasma.

The target polypeptide was indirectly fluorescently labeled by reacting a labeled antibody bound to Alexa Fluor (trademark) 647 or Alexa Fluor (trademark) 488 against the target polypeptide with each polypeptide contained in the specimen. Each polypeptide measured by FCCS was labeled with both Alexa Fluor (trademark) 647-labeled antibody and Alexa Fluor (trademark) 488-labeled antibody.

A fluorescently labeled antibody solution in the same amount as the specimen was added to serum or plasma. After adding the fluorescently labeled antibody, the mixture was mixed and incubated in the dark at room temperature for 5 minutes. Thereafter, it was centrifuged at 13,000 rpm/5 minutes, and the supernatant was used as a measurement sample.

3. Measurement (1) Measurement of Fluorescently Labeled Reference Polypeptide

When PBS was used as an aqueous solvent, each fluorescently labeled reference polypeptide directly labeled with the fluorescent dye was added to PBS to be 100 nM to prepare a standard sample for preparing a calibration curve. When a diluted specimen was used as an aqueous solvent, each fluorescently labeled reference polypeptide was added to serum or plasma to be 100 nM to prepare a standard sample for preparing a calibration curve.

30 µl of each standard sample was added to a 384-well glass bottom plate (Sigma-Aldrich, M4437-16EA) pre-blocked with a blocking reagent N101 (NOF, 71S410050011) and subjected to a measurement. Measurement was made on a Zeiss Axio Observer Confocor 3 setup with LSM710 laser module. Alexa Fluor (trademark) 488 was excited with a 488 nm laser. Alexa Fluor (trademark) 647 was excited with a 633 nm laser. The 488 nm and 633 nm lasers were output at 8 mW and 1.2 mW, respectively. One measurement was performed for 20 seconds for each well, and 10 measurements were performed. That is, a total measurement time per well was set to 200 seconds. Correlation function was calculated based on these 10 measurements. Temperature at the time of measurement was set to 23° C. Zeiss Zen software was used for FCS analysis and FCCS analysis.

(2) Fitting of Each Function and Size Estimation of Polypeptide

Raw data acquired using Zen software was preprocessed to remove a measured value that indicated baseline drift or burst (average fluorescence brightness and over three times higher fluorescence signal). Cross-correlation used in FCCS and fitting of an autocorrelation curve used in FCS were performed by one-component or two-component fitting based on a 3D diffusion model (3D, or 3D+3D, or T×3D, or T×{3D+3D}).

Fitting function $G(\tau)$ for obtaining a three-dimensional one-component correlation curve (3D) is represented by the following Eq. 1A. Fitting function $G(\tau)$ for obtaining a three-dimensional two-component correlation curve (3D+3D) is represented by the following Eq. 1B. Both functions represent a translational diffusion process. When calculating a translational diffusion time from a cross-correlation curve, a fitting model was used as in the following Eq. 1A or Eq. 1B.

[Expression 1]

$$G(t) = \frac{1}{\bar{N}}\left(1 + \frac{t}{\tau_D}\right)^{-1}\left(1 + \frac{t}{\omega^2 \tau_D}\right)^{-1/2} \quad \text{Eq. 1A}$$

[Expression 2]

$$G(t) = \frac{Q_1^2 \bar{N}_1}{(Q_1 \bar{N}_1 + Q_2 \bar{N}_2)^2}\left(1 + \frac{t}{\tau_{D1}}\right)^{-1}\left(1 + \frac{t}{\omega^2 \tau_{D1}}\right)^{-1/2} + \frac{Q_2^2 \bar{N}_2}{(Q_1 \bar{N}_1 + Q_2 \bar{N}_2)^2}\left(1 + \frac{t}{\tau_{D2}}\right)^{-1}\left(1 + \frac{t}{\omega^2 \tau_{D2}}\right)^{-1/2} \quad \text{Eq. 1B}$$

In Eq. 1A. N represents amplitude (number of molecules). TD indicates a diffusion time (µs), t indicates lag time, ω (structural factor) is a ratio (wz/wxy) of a horizontal (XY) width and a vertical (Z) axis width of a laser focal volume. In Eq. 1B, Q is a quantum yield.

Structural factors were assigned daily at the start of the measurement, based on known diffusion times obtained from a dye mixture of 100 nM Alexa Fluor (trademark) 488 and 10 nM Alexa Fluor (trademark) 647 used as a reference.

In order to calculate a triplet state transition time (τ), a fitting model was used as in Eq. 2 below.

The following Eq. 2 shows triplet state transition.

[Expression 3]

$$G(\tau) = \left(1 + \frac{T}{1-T}e^{\frac{-\tau}{\tau_T}}\right) \quad \text{Eq. 2}$$

In Eq. 2, τ indicates triplet state amplitude. $\tau_T$ indicates triplet state transition of dye fluorophore.

In the case of autocorrelation function, a fitting model was used as in Eq. 3 below, which included both the translational diffusion time and the triplet state transition time of the dye (T×3D or T×{3D+3D}).

[Expression 4]

$$G(\tau) = \prod_i G_i(\tau) \quad \text{Eq. 3}$$

Each of the above formulas is publicly known (Krichevsky and Bonnet, 2002. Fluorescent Correlation Spectroscopy, the technique and its applications. Rep. Prog. Phys. 65 251).

(i) FCS Analysis Using Specimens

In FCS, fitting of the autocorrelation function was performed with a two-component model. A first component was an unreacted fluorescently labeled antibody. A second component was each immune complex of each reference polypeptide and its corresponding fluorescently labeled antibody. First, a one-component model was selected on Zen software, and a diffusion time of the first component was measured for each fluorescently labeled antibody in another independent experimental system containing no antigen (Tp488 or Tp647). Next, a two-component model was selected on the Zen software, and a diffusion time of the first component was fixed to the previously measured diffusion time of the first component (Tp488 or Tp647). A diffusion time of the second component was measured. A regression equation for the acquired diffusion time and a hydrodynamic radius (nm) of each reference polypeptide was obtained, and a calibration curve was prepared.

Also, for a target polypeptide, a diffusion time was obtained in the same manner as that for the reference polypeptide, and a hydrodynamic radius was calculated from a calibration curve.

(ii) FCCS Analysis Using Diluted Specimen

In FCCS, fitting of the correlation function was performed with a one-component model. One component is each immune complex of each polypeptide and its corresponding fluorescently labeled antibody. A one-component model was selected on Zen software, and a diffusion time of each immune complex was measured. A regression equation for the acquired diffusion time and a hydrodynamic radius (nm) of each reference polypeptide was obtained, and a calibration curve was prepared. Also, for a target polypeptide, a diffusion time was obtained in the same manner as that for the reference polypeptide, and a hydrodynamic radius was calculated from a calibration curve.

II. Comparative Example 1

Figure 3:
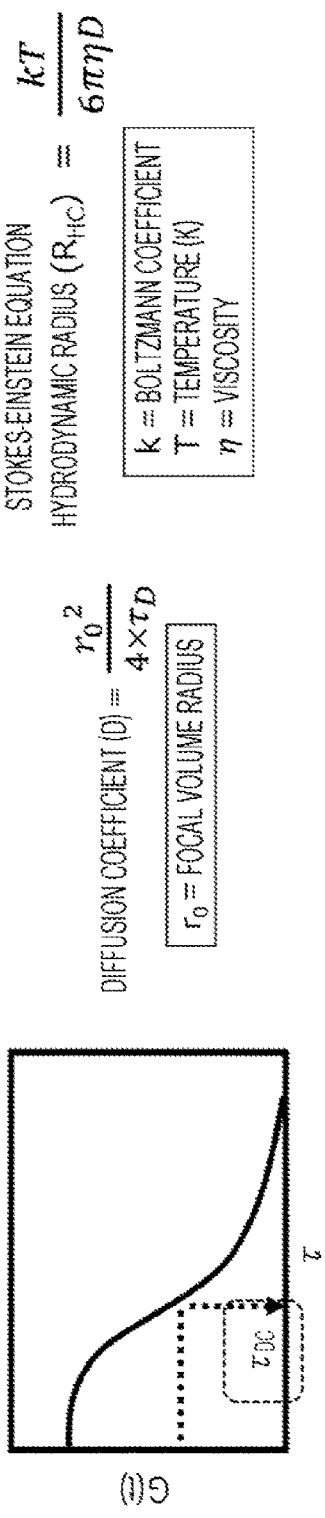
FIG. 3 shows an outline of proportional conversion used in Comparative Example 1.
Figure 3:
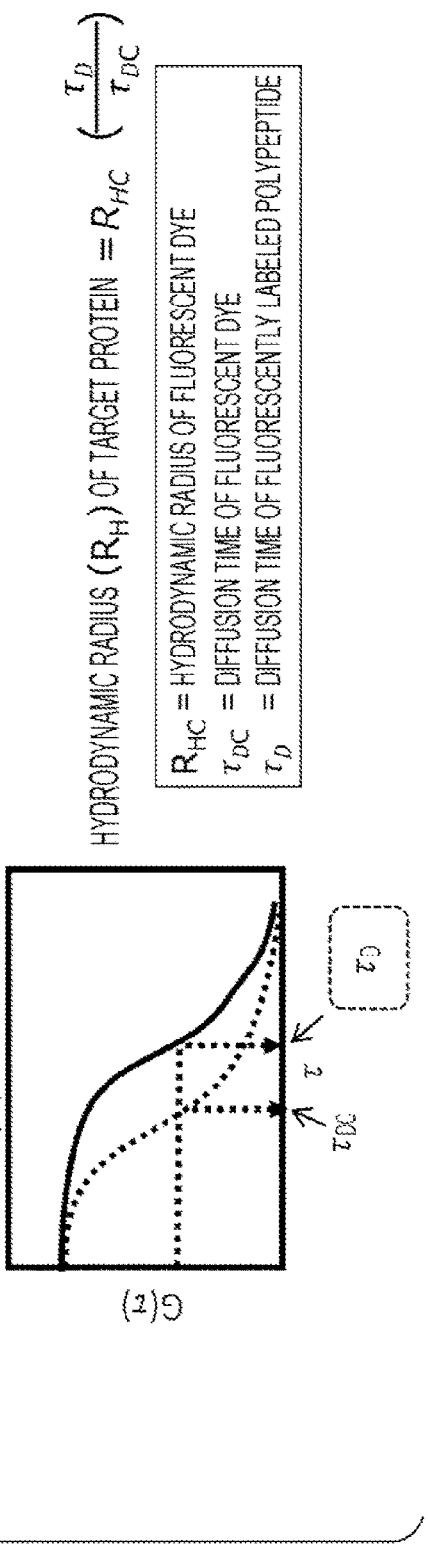

As Comparative Example 1, the proportional conversion described in Non-Patent Document 1 was used. FIG. 3 shows an outline of proportional conversion. In the proportional conversion, first, a diffusion time of Alexa Fluor (trademark) 488 (hydrodynamic radius $R_{HC}$=0.7 nm) with a known hydrodynamic radius $R_{HC}$ as a standard, and a diffusion time of Alexa Fluor (trademark) 647 (hydrodynamic radius R=0.8 nm) were measured by FCS (Step 1 in FIG. 3). Temperature at the time of measurement was set to 23° C. Subsequently, autocorrelation function of the standard was obtained, and the diffusion time of the fluorescent dye was corrected (Step 2 in FIG. 3). Subsequently, the diffusion time of the fluorescently labeled target polypeptide was measured by FCS, and hydrodynamic radius $R_H$ of the fluorescently labeled target polypeptide was determined from the diffusion time $\tau_{DC}$ (μs) of the fluorescent dye, the diffusion time $\tau_D$ (μs) of the fluorescently labeled target polypeptide, and the hydrodynamic radius $R_{HC}$ as the standard.

III. Example 1

A diffusion time was measured by FCCS, according to the method described in I, above, using PBS or diluted specimen as an aqueous solvent, and Aprotinin, lysozyme, CA, BSA, pi-Amylase, Apo-ferritin, and Thyroglobulin as reference polypeptides, and a calibration curve was prepared. A calibration curve was prepared, using 1 example of serum and 2 examples of plasma from different subjects as specimens.

Figure 4A:
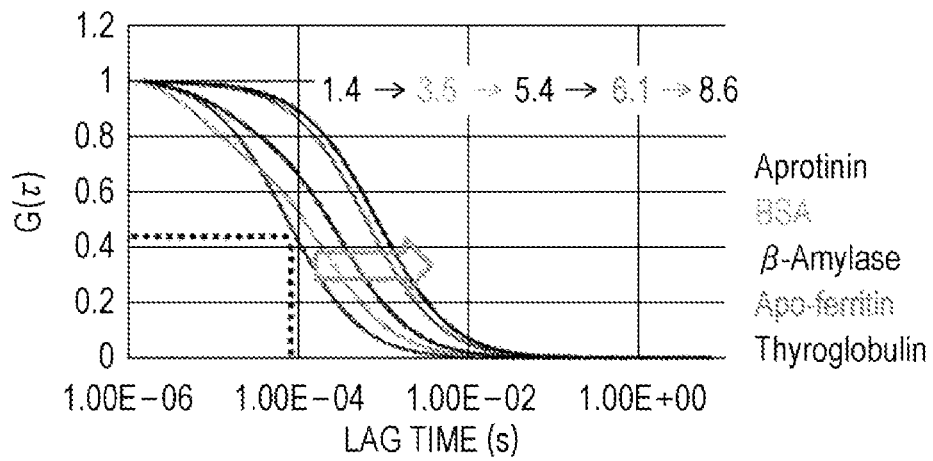
FIG. 4A shows a result after measuring and standardizing hydrodynamic radius in PBS.
Figure 4B:
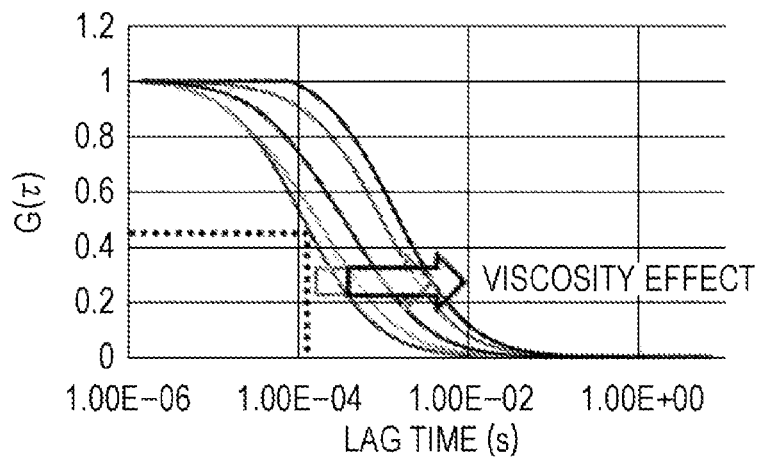
FIG. 4B shows a result after measuring and standardizing hydrodynamic radius in diluted plasma.
Figure 4C:
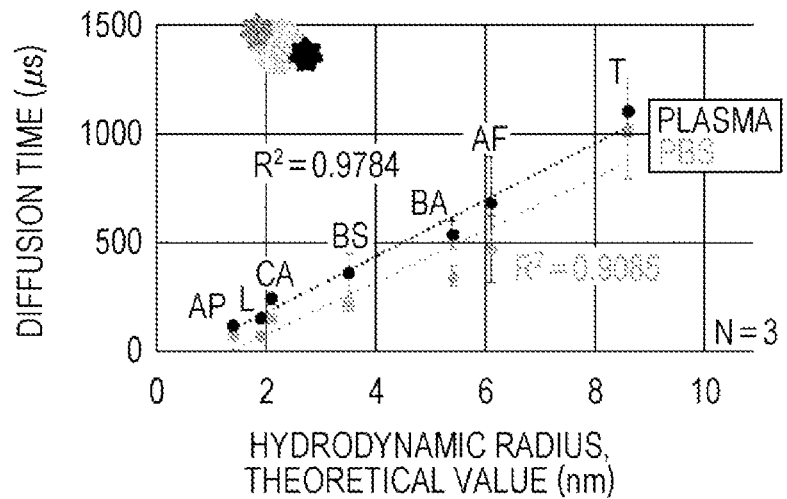
FIG. 4C shows difference in calibration curves between a case of using PBS and a case of using a diluted specimen as an aqueous solvent.

FIG. 4 shows a difference in diffusion times (lag time(s)) between a case of using PBS and a case of using diluted plasma as an aqueous solvent. FIG. 4A shows results after measuring and standardizing the hydrodynamic radius in the PBS. FIG. 4B shows results after measuring and standardizing the hydrodynamic radius in the diluted plasma. In FIG. 4B, the correlation curve was shifted to right as compared with FIG. 4A. FIG. 4C shows a difference in calibration curves between a case of using PBS and a case of using diluted plasma as an aqueous solvent. Slopes of the calibration curves were not different between the case of using PBS and the case of using diluted plasma as the aqueous solvent, but a Y-intercept was lower in PBS. From this, it was shown that the molecular diffusion rate is slower in diluted plasma that has a higher viscosity than that of PBS.

Figure 5A:
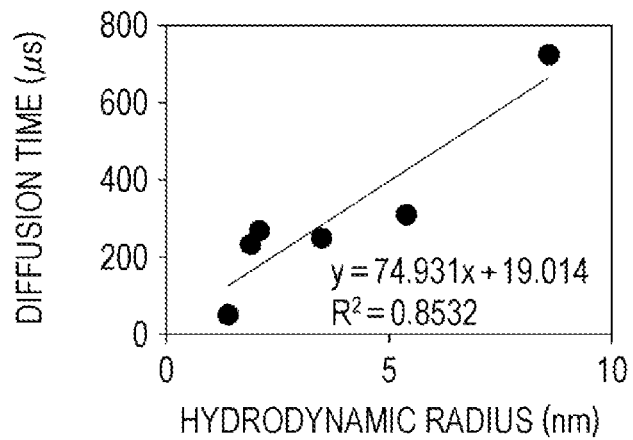
FIG. 5A is a calibration curve prepared based on a diffusion time measured using diluted serum.
Figure 5B:
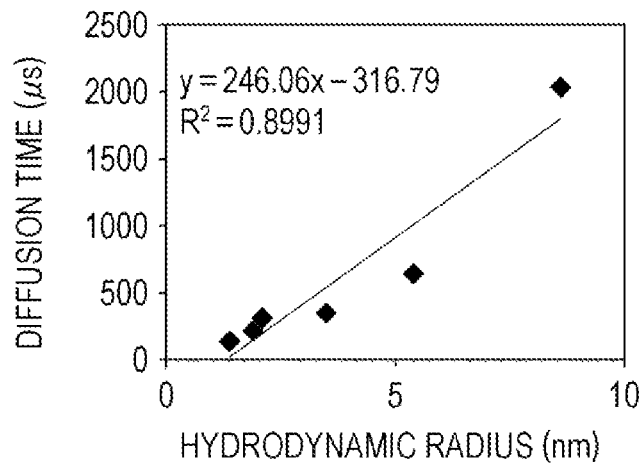
FIG. 5B is a calibration curve prepared based on a diffusion time measured using a diluted plasma 1.
Figure 5C:
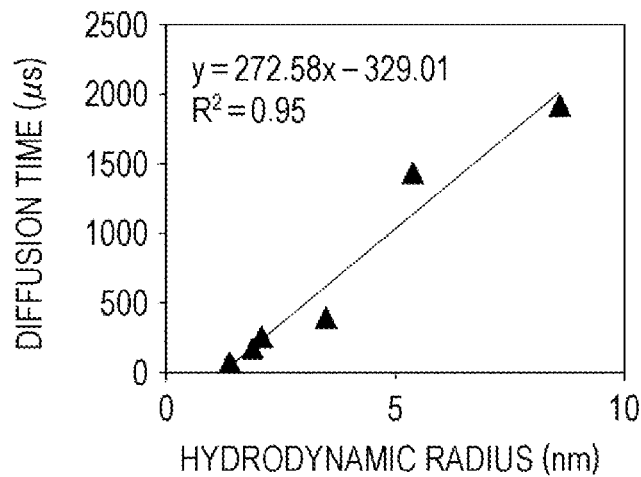
FIG. 5C is a calibration curve prepared based on a diffusion time measured using a diluted plasma 2 different from the diluted plasma 1.

FIG. 5 shows calibration curves acquired using three different types of specimens. FIG. 5A is a calibration curve prepared based on a diffusion time measured using diluted serum. FIG. 5B is a calibration curve prepared based on a diffusion time measured using diluted plasma 1. FIG. 5C is a calibration curve prepared based on a diffusion time measured using diluted plasma 2 different from diluted plasma 1. As compared to the plasma, the serum had a shorter diffusion time. It was also shown that the diffusion time of plasma differs depending on the specimen.

From these results, in order to predict size of the target polypeptide, it was considered preferable to measure the reference polypeptide in the solvent environment equivalent to the target polypeptide and prepare a calibration curve.

Figures 6A, 6B:
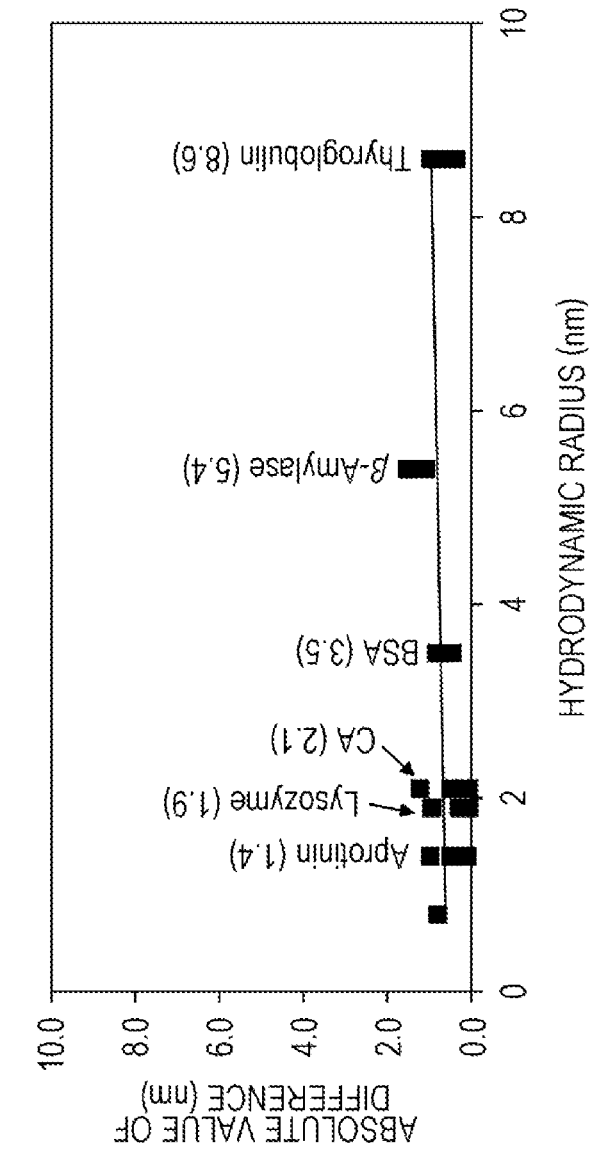
FIG. 6A shows values of the difference between predicted values and theoretical values of size obtained for β-Amylase by the method of the present invention.
FIG. 6B relates an absolute value of the difference between a predicted value and a theoretical value obtained for the size of each reference polypeptide to the hydrodynamic radius of the reference polypeptide.

Assuming that each of the reference polypeptides was a target polypeptide, a predicted value of the hydrodynamic radius of each reference polypeptide was calculated based on the calibration curve obtained by a measurement system using the diluted specimen of FCCS of the present disclosure. As the specimen, serum, plasma 1 or plasma 2 was used. Then, by using a molecular size described as a gel filtration chromatography marker as a theoretical value of the hydrodynamic radius, a difference between the predicted value and the theoretical value and an absolute value of the difference were obtained. FIG. 6A shows values of differences obtained for D-Amylase. FIG. 6B shows a relationship between an absolute value of a difference obtained for each reference polypeptide and a hydrodynamic radius of the reference polypeptide in each specimen.

Figures 7A, 7B:
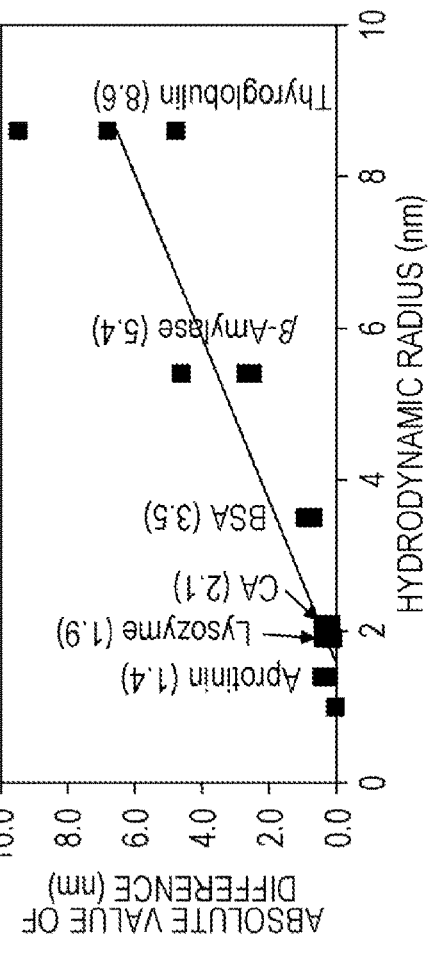
FIG. 7A shows values of the difference in hydrodynamic radius (nm) between predicted values and theoretical values obtained for β-Amylase by the method of Comparative Example 1.
FIG. 7B shows the relationship between an absolute value of the difference (nm) obtained for each reference polypeptide and the molecular size of the reference polypeptide in each specimen.

Predicted values of the reference polypeptides were calculated in the same manner, according to the method of Comparative Example 1, and compared with theoretical values of each reference polypeptide. The results are shown in FIG. 7. FIG. 7A shows values of differences between the predicted values and the theoretical values obtained for β-Amylase. FIG. 7B shows a relationship between an absolute value of a difference obtained for each reference polypeptide and a molecular size of the reference polypeptide in each specimen. In the method described in Comparative Example 1, the difference between the predicted value and the theoretical value was large even when the fluorescent dyes of Alexa Fluor (trademark) 488 and Alexa Fluor (trademark) 647 were used as the standard. The difference between the predicted value and the theoretical value was large even when any of the three types of specimens was used. In particular, it was shown that the larger the hydrodynamic radius of the reference peptide, the larger the difference between the predicted value and the theoretical value.

From these results, it was shown that the information acquisition method of the present disclosure has higher prediction accuracy than the comparative example.

IV. Example 2

In order to prove that, for large-sized polypeptides, a hydrodynamic radius can be predicted by the information acquisition method of the present disclosure, a molecular size of von Willebrand factor (VWF; molecular weight about 250 kDa) was predicted according to the information acquisition method of the present disclosure using FCCS.

As a positive sample, a sample was prepared by adding a recombinant VWF protein (Merck, 681300-100UGCN) to plasma at a final concentration of 25 nM. As a negative sample, a sample was prepared by adding a buffer in the same amount as the recombinant VWF protein solution to plasma, without adding the recombinant VWF protein. The positive sample and the negative sample were subjected to the same treatment as shown below.

Alexa Fluor (trademark) 488-labeled 2F2A9 antibody (BD Biosciences, 555849) and Alexa Fluor (trademark) 647-labeled NMC4 Fab were added to each sample at a final concentration of 100 nM, respectively, and reacted at room temperature in the dark for 5 minutes. NMC4 Fab was prepared by gene recombination from a known amino acid sequence of NMC4 Fab.

FCCS was measured according to the method described in 3. above.

Figures 8A, 8B:
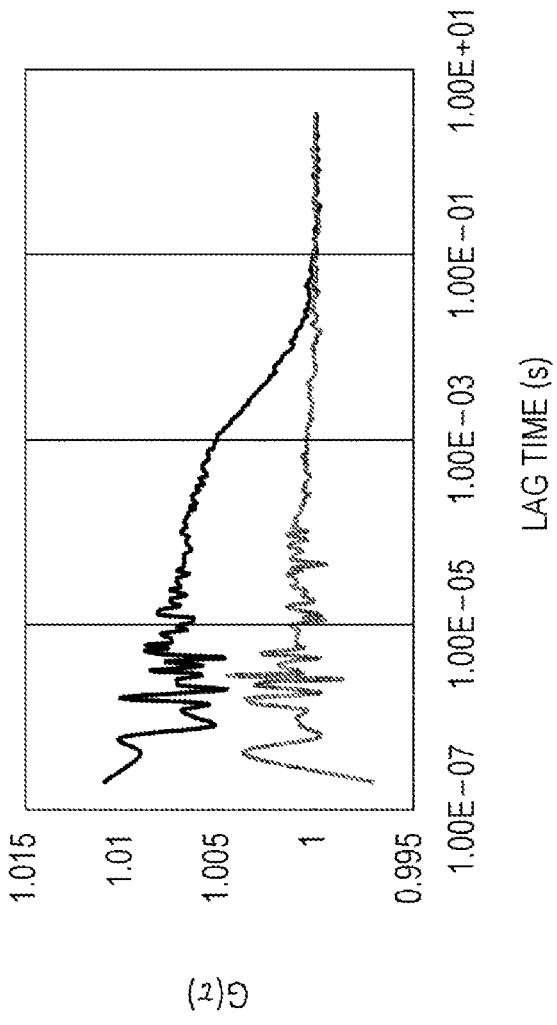
FIG. 8A shows cross-correlation G(τ) and lag time before standardization when recombinant VWF protein was measured by FCCS.
FIG. 8B shows a predicted value and a theoretical value of the size (nm) of the recombinant VWF protein calculated based on the method of the present invention, and the difference between thereof.

The results are shown in FIG. 8. FIG. 8A shows cross-correlation G(τ) and lag time before standardization. FIG. 8B shows a predicted value and a theoretical value of the size of the recombinant VWF protein calculated based on the information acquisition method of the present disclosure, and a difference between thereof calculated.

The theoretical value of the hydrodynamic radius of the recombinant VWF protein is 16.25 nm in a state unreacted with the antibody, which is a relatively large protein. It was shown that, even with such a large protein, the difference between the predicted value and the measured value is as small as 2.3 nm, indicating that accurate prediction is possible.

V. Example 3

In order to prove that, for small-sized polypeptides, a hydrodynamic radius can be predicted by the information acquisition method of the present disclosure, a hydrodynamic radius of hen egg white lysozyme (molecular weight of about 14 kDa; hydrodynamic radius of 3 nm) was predicted according to the information acquisition method of the present disclosure using FCCS.

As a positive sample, a sample was prepared by adding hen egg white lysozyme protein (Sigma-Aldrich, L4919-500 MG) to plasma at a final concentration of 100 nM. As a negative sample, a sample was prepared by adding a buffer in the same amount as the hen egg white lysozyme protein solution to plasma, without adding the hen egg white lysozyme protein. The positive sample and the negative sample were subjected to the same treatment as shown below.

Alexa Fluor (trademark) 488-labeled cAB-Lys2 VHH and Alexa Fluor (trademark) 647-labeled D2L24 VHH were added to each sample at a final concentration of 100 nM, respectively, and reacted at room temperature in the dark for 5 minutes, cAB-Lys2 VHH and D2L24 VHH were prepared by gene recombination from known amino acid sequences of cAB-Lys2 VHH and D2L24 VHH, respectively.

FCCS was measured according to the method described in 3. above.

Figures 9A, 9B:
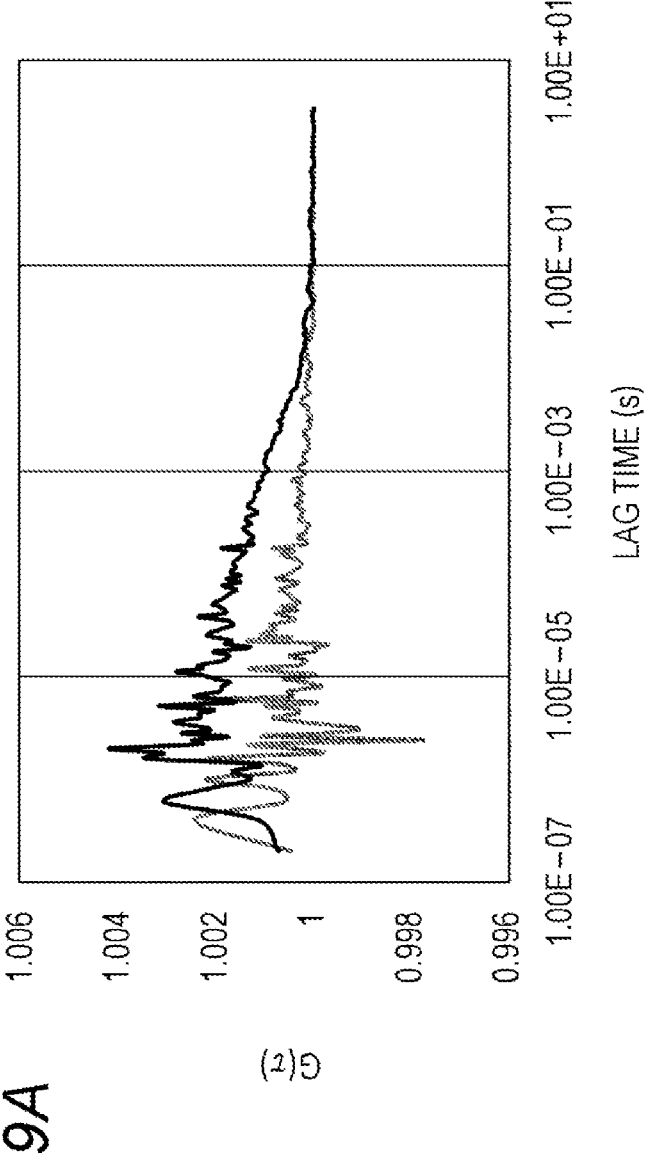
FIG. 9A shows cross-correlation G(τ) and lag time before standardization when hen egg white lysozyme was measured by FCCS.
FIG. 9B shows a predicted value and a theoretical value of the size (nm) of the hen egg white lysozyme protein calculated based on the method of the present invention, and the difference between thereof.

The results are shown in FIG. 9. FIG. 9A shows cross-correlation G(τ) and lag time before standardization. FIG. 9B shows a predicted value and a theoretical value of the size of the hen egg white lysozyme protein calculated based on the information acquisition method of the present disclosure, and a difference between thereof.

The theoretical value of the hydrodynamic radius of the hen egg white lysozyme protein is 3 nm in a state unreacted with the antibody, which is a relatively small protein. It was shown that, even with such a small protein, the difference between the predicted value and the measured value is as small as 0.5 nm, indicating that accurate prediction is possible.

VI. Example 4 and Comparative Example 2

In the measurement system using PBS as the aqueous solvent, prediction accuracy was evaluated when the information acquisition method of the present disclosure was carried out by FCCS.

Figures 10A, 10B:
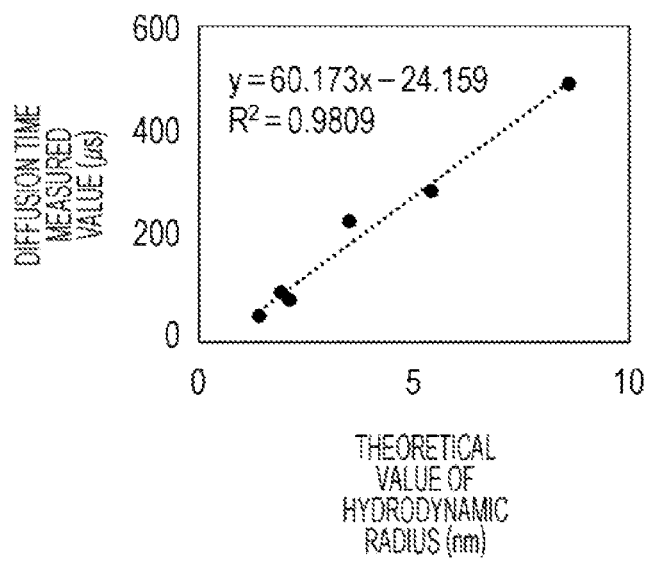
FIG. 10A shows diffusion times (μs) and theoretical values of hydrodynamic radius (nm) of each reference polypeptide when measured by FCCS using PBS as an aqueous solvent.
FIG. 10B shows a calibration curve prepared based on FIG. 10A.

In Example 4, using the FCCS measurement system using PBS as the aqueous solvent described in 3. above, a calibration curve was prepared using the reference polypeptide double-labeled with the two-color fluorescent dyes described above. Assuming that each of the reference polypeptides was a target polypeptide, a hydrodynamic radius of each of the reference polypeptides was determined from the calibration curve. FIG. 10A shows diffusion times (μs) and theoretical values of hydrodynamic radius of each reference polypeptide in FCCS. FIG. 10B shows a calibration curve prepared based on FIG. 10A. FIG. 10C shows absolute values of differences between predicted values and theoretical values of hydrodynamic radius and accuracy obtained in Example 4. The accuracy (%) was calculated by subtracting % error from 100%. The % error was obtained by formula of 100×[(absolute value of difference)/(theoretical value)].

In Comparative Example 2, the hydrodynamic radius was predicted by the proportional conversion described in Non-Patent Document 1 in the same manner as in Comparative Example 1 using the diffusion time measured value $\tau_{DC}$ measured by FCCS. However, as a standard. BSA bound with Alexa Fluor (trademark) 647-labeled anti-BSA antibody and Alexa Fluor (trademark) 488-labeled anti-BSA antibody instead of the fluorescent dyes was used so that the measurement could be performed by FCCS. The measurement system used PBS as an aqueous solvent. The double fluorescent labeled BSA has a hydrodynamic radius $R_{HC}$ of 3.5 nm and a diffusion time measured value DC of 230 μs. Assuming that each of the double-fluorescently labeled reference polypeptides was a target polypeptide, a hydrodynamic radius of each of the reference polypeptides was determined according to the method of Comparative Example 1. FIG. 10D shows absolute values of differences between predicted values and theoretical values of hydrodynamic radius and accuracy obtained in Comparative Example 2. Definitions of terms are the same as in FIG. 10C.

In Comparative Example 2, since BSA was used as the standard, the absolute value of the difference was 0 and the prediction accuracy was 100%, but other than that, the accuracy of Example 4 was higher.

VII. Example 5, Reference Example and Comparative Example 3

In the measurement system using PBS as the aqueous solvent, prediction accuracy when the information acquisition method of the present disclosure was carried out by FCS was evaluated.

Figures 11A, 11B:
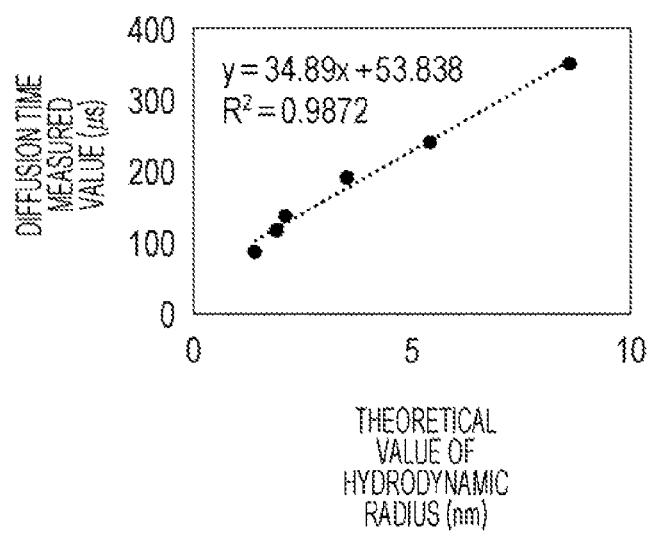
FIG. 11A shows diffusion times (μs) and theoretical values of hydrodynamic radius of each reference polypeptide measured by FCS using PBS as an aqueous solvent.
FIG. 11B shows a calibration curve prepared based on FIG. 11A.

In Example 5, using the FCS measurement system with PBS as the aqueous solvent described in 3. above, a calibration curve was prepared using the reference polypeptide labeled with the two-color fluorescent dyes described above. Assuming that each of the reference polypeptides was a target polypeptide, a hydrodynamic radius of each of the reference polypeptides was determined from the calibration curve. FIG. 11A shows diffusion times (μs) and theoretical values of hydrodynamic radius of each reference polypeptide in FCS. FIG. 11B shows a calibration curve prepared based on FIG. 11A.

Figure 11C:
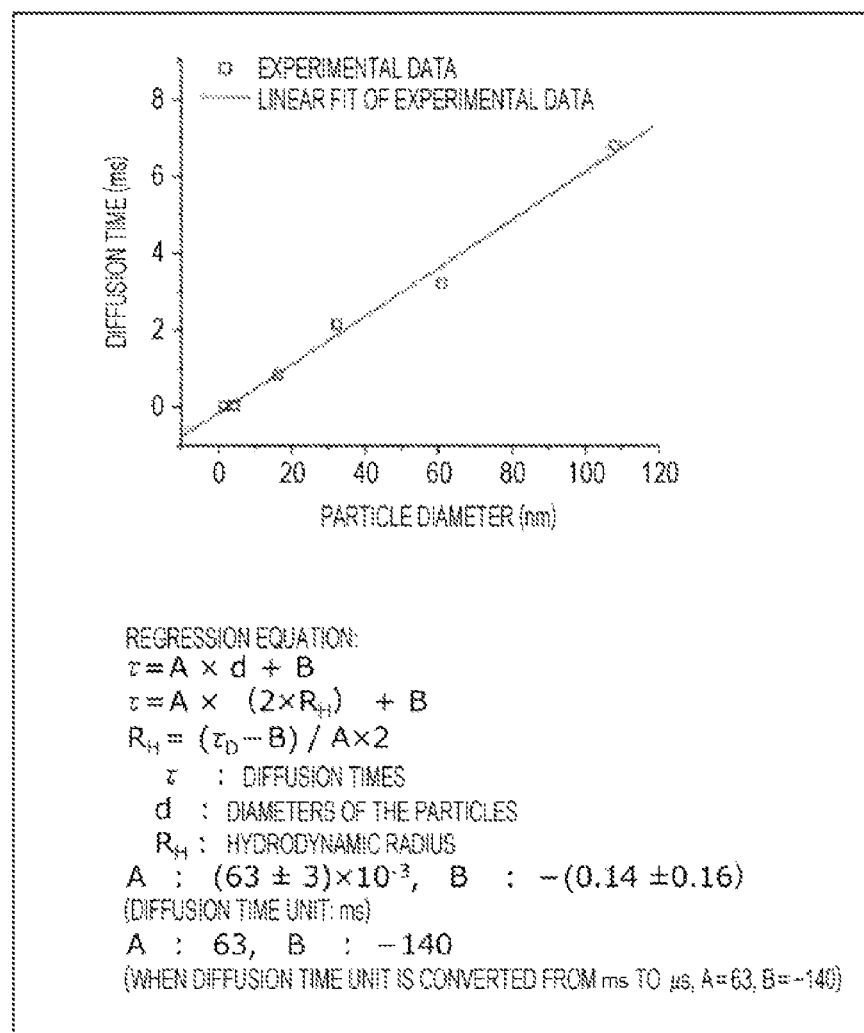
FIG. 11C shows a calibration curve and regression equations obtained by Reference Example.

Reference Example is an example measured by a method using fluorescent beads as the calibrator described in Non-Patent Document 2. As shown in FIG. 11C, a diffusion time (msec) of fluorescent beads of various particle sizes was measured by FCS, a regression equation was prepared based on the diffusion time and particle size, and the diffusion time of the fluorescently labeled target polypeptide measured by FCS was applied to the regression equation. The hydrodynamic radius was determined assuming that each of the reference polypeptides reacted with Alexa Fluor (trademark) 647-labeled antibody was a target polypeptide.

Comparative Example 3 is an example in which the hydrodynamic radius was determined by the same method as in Comparative Example 1 described in II. As the standard, Alexa Fluor (trademark) 647 dye was used. The measurement system used PBS as an aqueous solvent. The Alexa Fluor (trademark) 647 dye has a hydrodynamic radius $R_{HC}$ of 0.8 nm and a diffusion time measured value $\tau_{DC}$ of 49 μs. Assuming that each of the fluorescently labeled reference polypeptides was a target polypeptide, a hydrodynamic radius of each of the reference polypeptides was determined according to the method of Comparative Example 1.

FIG. 12A shows a result of Example 5, FIG. 12B shows a result of Reference Example, and FIG. 12C shows a result of Comparative Example 3. Example 5 showed good accuracy in a range of reference polypeptides used. It was shown that in Reference Example and Comparative Example 3, the accuracy in a range where the hydrodynamic radius is large is poor as compared with that in Example 5, and the hydrodynamic radius tends to be shown smaller than actual.

Figure 13A:
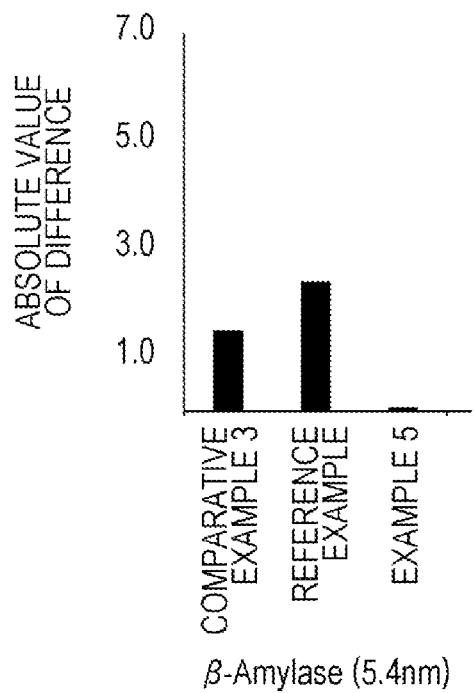
FIG. 13A shows a comparison data of absolute values of difference between predicted values and diffusion times for β-Amylase.
Figure 13B:
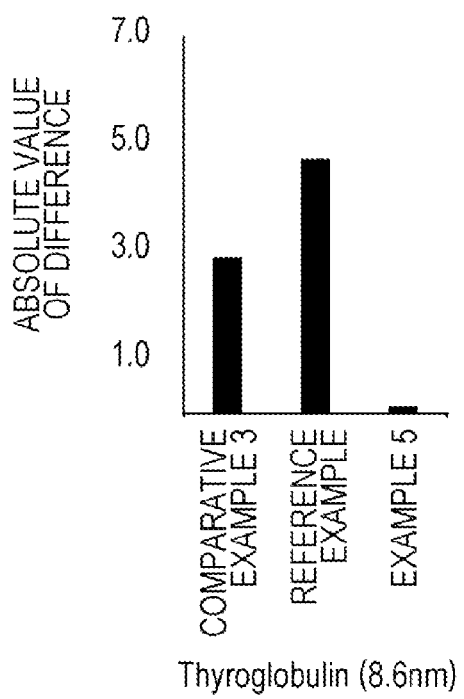
FIG. 13B shows a comparison data of absolute values of difference in Thyroglobulin.

FIG. 13A shows a comparison data of absolute values of differences between predicted and theoretical values for β-Amylase. FIG. 13B shows a comparison data of absolute values of differences for Thyroglobulin. In Example 5, the absolute values of differences were smaller in both polypeptides than those in Reference Example and Comparative Example 3.

Abnormal proteins may have a larger hydrodynamic radius than normal proteins. In such a case, in the methods described in Non-Patent Document 1 and Non-Patent Document 2, it is considered that a hydrodynamic radius of the abnormal protein is estimated to be smaller than actual, and there is a risk of false negative.

What is claimed is:

1. A method for acquiring information of a target polypeptide, comprising:
   acquiring a diffusion time of a fluorescently labeled target polypeptide and a diffusion time of each of a plurality of fluorescently labeled reference polypeptides by fluorescence correlation spectroscopy or fluorescence cross-correlation spectroscopy, and
   acquiring information on size of the fluorescently labeled target polypeptide from the diffusion time of the fluorescently labeled target polypeptide with reference to the diffusion times of the plurality of fluorescently labeled reference polypeptides,
   wherein information on size of each of the plurality of fluorescently labeled reference polypeptides is known,
   the sizes of the plurality of reference polypeptides are different from each other;
   the plurality of fluorescently labeled reference polypeptides comprises: a fluorescently labeled first reference polypeptide, which is a first reference polypeptide labeled with a fluorescent dye; and a fluorescently labeled second reference polypeptide, which is a second reference polypeptide labeled with the same fluorescent dye as the fluorescent dye of the fluorescently labeled first reference polypeptide,
   the fluorescently labeled first reference polypeptide and the fluorescently labeled second reference polypeptide are different in size from each other,
   before the step of acquiring diffusion time, dividing a specimen containing the target polypeptide collected from a living body into at least a first aliquot, a second aliquot and a third aliquot, fluorescently labeling the target polypeptide contained in the first aliquot to prepare the fluorescently labeled target polypeptide, mixing the second aliquot and the fluorescently labeled first reference polypeptide, and mixing the third aliquot and the fluorescently labeled second reference polypeptide,
   in the step of acquiring diffusion time, a diffusion time of the fluorescently labeled target polypeptide in the first aliquot, a diffusion time of the fluorescently labeled first reference polypeptide in the second aliquot and a diffusion time of the fluorescently labeled second reference polypeptide in the third aliquot are acquired, and
   in the step of acquiring the information, information on size of the fluorescently labeled target polypeptide is acquired from the diffusion time of the fluorescently labeled target polypeptide with reference to the diffusion time of the fluorescently labeled first reference polypeptide and the diffusion time of the fluorescently labeled second reference polypeptide.

2. The method for acquiring information of the target polypeptide according to claim 1, wherein the size is a hydrodynamic radius, a hydrodynamic diameter, or a volume.

3. The method for acquiring information of the target polypeptide according to claim 1, wherein a hydrodynamic radius of each of the reference polypeptides is 1 nm or more and 20 nm or less.

4. The method for acquiring information of the target polypeptide according to claim 1, wherein
   the first reference polypeptide has a hydrodynamic radius of 1 nm or more and less than 5 nm, and
   the second reference polypeptide has a hydrodynamic radius of 5 nm or more and 10 nm or less.

5. The method for acquiring information of the target polypeptide according to claim 1, wherein the hydrodynamic radius of the first reference polypeptide is at least twice the hydrodynamic radius of the second reference polypeptide.

6. The method for acquiring information of the target polypeptide according to claim 1, wherein
   the plurality of fluorescently labeled reference polypeptides further comprises: a fluorescently labeled third reference polypeptide, which is a third reference polypeptide labeled with the same fluorescent dye as the fluorescent dye of the fluorescently labeled first reference polypeptide,
   the fluorescently labeled first reference polypeptide, the fluorescently labeled second reference polypeptide and the fluorescently labeled third reference polypeptide are different in size from each other,
   in the step of acquiring diffusion time, the diffusion time of the fluorescently labeled first reference polypeptide, the diffusion time of the fluorescently labeled second reference polypeptide and a diffusion time of the fluorescently labeled third reference polypeptide are acquired, and in the step of acquiring information, information on size of the fluorescently labeled target polypeptide is acquired from the diffusion time of the fluorescently labeled target polypeptide with reference to the diffusion time of the fluorescently labeled first reference polypeptide, the diffusion time of the fluorescently labeled second reference polypeptide and the diffusion time of the fluorescently labeled third reference polypeptide.

7. The method for acquiring information of the target polypeptide according to claim 6, wherein
the first reference polypeptide has a hydrodynamic radius of 1 nm or more and less than 3 nm,
the second reference polypeptide has a hydrodynamic radius of 3 nm or more and less than 6 nm, and
the third reference polypeptide has a hydrodynamic radius of 6 nm or more and less than 9 nm.

8. The method for acquiring information of the target polypeptide according to claim 1, wherein,
in the fluorescently labeled target polypeptide, a fluorescent dye is chemically bound to the target polypeptide, and
in the fluorescently labeled reference polypeptide, a fluorescent dye is chemically bound to the reference polypeptide.

9. The method for acquiring information of the target polypeptide according to claim 8, wherein the chemical bond is a covalent bond.

10. The method for acquiring information of the target polypeptide according to claim 1, wherein,
in the fluorescently labeled target polypeptide, the fluorescent dye is bound to the target polypeptide via an antibody, and
in the fluorescently labeled reference polypeptide, the fluorescent dye is bound to the reference polypeptide via an antibody.

11. The method for acquiring information of the target polypeptide according to claim 10, further comprising, before the step of acquiring the diffusion time, preparing the fluorescently labeled target polypeptide by reacting the target polypeptide with a fluorescently labeled antibody that recognizes the target polypeptide.

12. The method for acquiring information of the target polypeptide according to claim 1, wherein, in the step of acquiring information, a calibration curve is prepared from the diffusion times of the plurality of fluorescently labeled reference polypeptides, and information on size of the fluorescently labeled target polypeptide is acquired based on the calibration curve.

13. The method for acquiring information of the target polypeptide according to claim 1 collected from the living body, and the specimen is whole blood, plasma, serum, cerebrospinal fluid, or urine.

14. The method for acquiring information of the target polypeptide according to claim 1, wherein
the step of acquiring diffusion time is performed by fluorescence cross-correlation spectroscopy, and
the fluorescently labeled target polypeptide contains two types of fluorescent dyes with different fluorescence wavelengths, and each of the plurality of fluorescently labeled reference polypeptides contains the two types of fluorescent dyes.

15. The method for acquiring information of the target polypeptide according to claim 14, wherein the fluorescently labeled target polypeptide is a complex of the target polypeptide, a first antibody containing a first fluorescent dye, and a second antibody containing a second fluorescent dye having a fluorescence wavelength different from that of the first fluorescent dye.

* * * * *